United States Patent
Weibler et al.

(10) Patent No.: US 8,993,898 B2
(45) Date of Patent: Mar. 31, 2015

(54) MOVABLE EMF SHIELD, METHOD FOR FACILITATING RAPID IMAGING AND TREATMENT OF PATIENT

(71) Applicants: Joseph C Weibler, West Chicago, IL (US); Thomas W Orzechowski, Carol Stream, IL (US); Steven T Kilgore, South Elgin, IL (US); Michael G Hamouz, Lisle, IL (US)

(72) Inventors: Joseph C Weibler, West Chicago, IL (US); Thomas W Orzechowski, Carol Stream, IL (US); Steven T Kilgore, South Elgin, IL (US); Michael G Hamouz, Lisle, IL (US)

(73) Assignee: ETS-Lindgren Inc., Wood Dale, IL (US)

( * ) Notice: Subject to any disclaimer, the term of this patent is extended or adjusted under 35 U.S.C. 154(b) by 94 days.

(21) Appl. No.: 13/911,885

(22) Filed: Jun. 6, 2013

(65) Prior Publication Data
US 2014/0003023 A1   Jan. 2, 2014

Related U.S. Application Data

(60) Provisional application No. 61/664,276, filed on Jun. 26, 2012.

(51) Int. Cl.
| | | |
|---|---|---|
| H01R 4/00 | (2006.01) | |
| H05K 9/00 | (2006.01) | |
| G01R 33/422 | (2006.01) | |
| A61B 5/00 | (2006.01) | |
| G01R 33/48 | (2006.01) | |
| A61B 5/055 | (2006.01) | |
| A61N 5/10 | (2006.01) | |

(52) U.S. Cl.
CPC ............ *H05K 9/0003* (2013.01); *G01R 33/422* (2013.01); *A61B 5/0046* (2013.01); *G01R 33/4808* (2013.01); *A61B 5/055* (2013.01); *A61N 2005/1055* (2013.01)
USPC .............................. 174/365; 174/375; 49/164

(58) Field of Classification Search
CPC ....................................................... H05K 9/0003
USPC ..................................... 174/365, 375; 49/164
See application file for complete search history.

(56) References Cited

U.S. PATENT DOCUMENTS

| | | | | |
|---|---|---|---|---|
| 5,452,550 | A | * | 9/1995 | Vanesky et al. ............... 52/173.1 |
| 5,569,878 | A | | 10/1996 | Zielinski |
| 5,736,671 | A | * | 4/1998 | Perala et al. ................... 174/365 |
| 5,786,547 | A | * | 7/1998 | Zielinski ........................ 174/375 |
| 6,061,961 | A | * | 5/2000 | Rupe ................................ 49/164 |
| 6,111,192 | A | * | 8/2000 | Bell et al. ....................... 174/384 |
| 6,225,554 | B1 | * | 5/2001 | Trehan et al. .................. 174/371 |

(Continued)

*Primary Examiner* — Hung V Ngo
(74) *Attorney, Agent, or Firm* — Cherskov, Flaynik & Gurda, LLC

(57) ABSTRACT

A radio frequency shield which reversibly transects an electromagnetic frequency enclosure is provided. The shield includes first a number of panels attached to a first surface of the enclosure. The panels are adapted to move through a first arc relative to the first surface. Shield also includes a first panel from the number of panels having a first leading edge capable of transecting the first arc. The shield further includes a second number of panels attached to a second surface of the enclosure. The second set of panels is adapted to move through an arc relative to the second surface of the enclosure. Also a second panel from said second set of panels has a second leading edge capable of transecting the second arc so as to oppose the first leading edge. Finally, the shield includes a means for reversibly attaching the first leading edge to the second leading edge while simultaneously establishing electrical communication between the first and second plurality of panels.

9 Claims, 19 Drawing Sheets

(56) References Cited

U.S. PATENT DOCUMENTS

| | | |
|---|---|---|
| 6,385,055 B1 * | 5/2002 | Kramer et al. ................ 361/816 |
| 6,422,287 B1 * | 7/2002 | Wilke ............................ 160/92 |
| 6,426,458 B1 * | 7/2002 | Hinzpeter et al. ............ 174/375 |
| 7,081,587 B1 * | 7/2006 | Woolsey ....................... 174/365 |
| 8,484,895 B2 * | 7/2013 | Kuhnmuench ................. 49/164 |
| 2002/0139053 A1 * | 10/2002 | Wright ............................ 49/383 |
| 2013/0199096 A1 * | 8/2013 | Moynihan et al. .............. 49/381 |

* cited by examiner

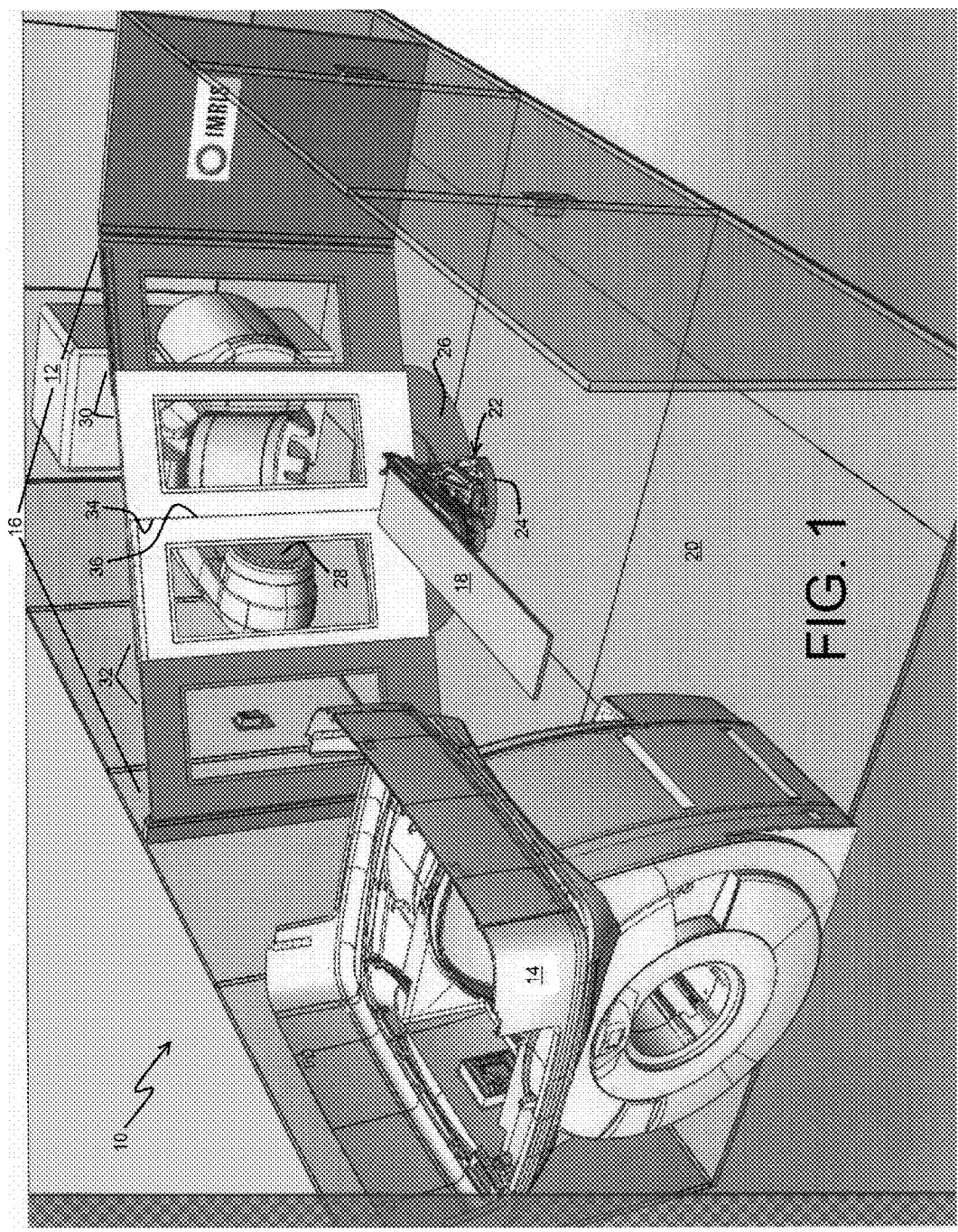

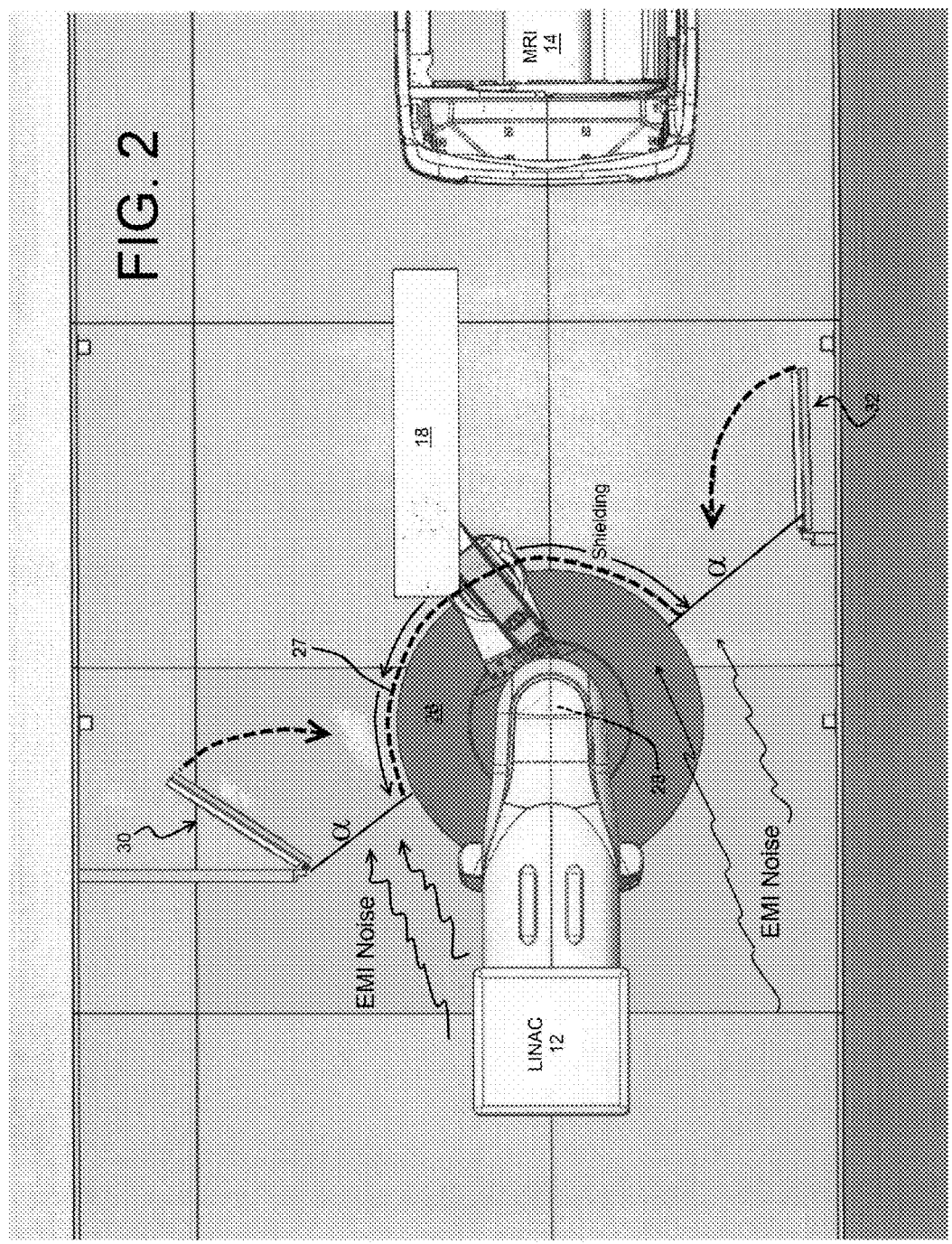

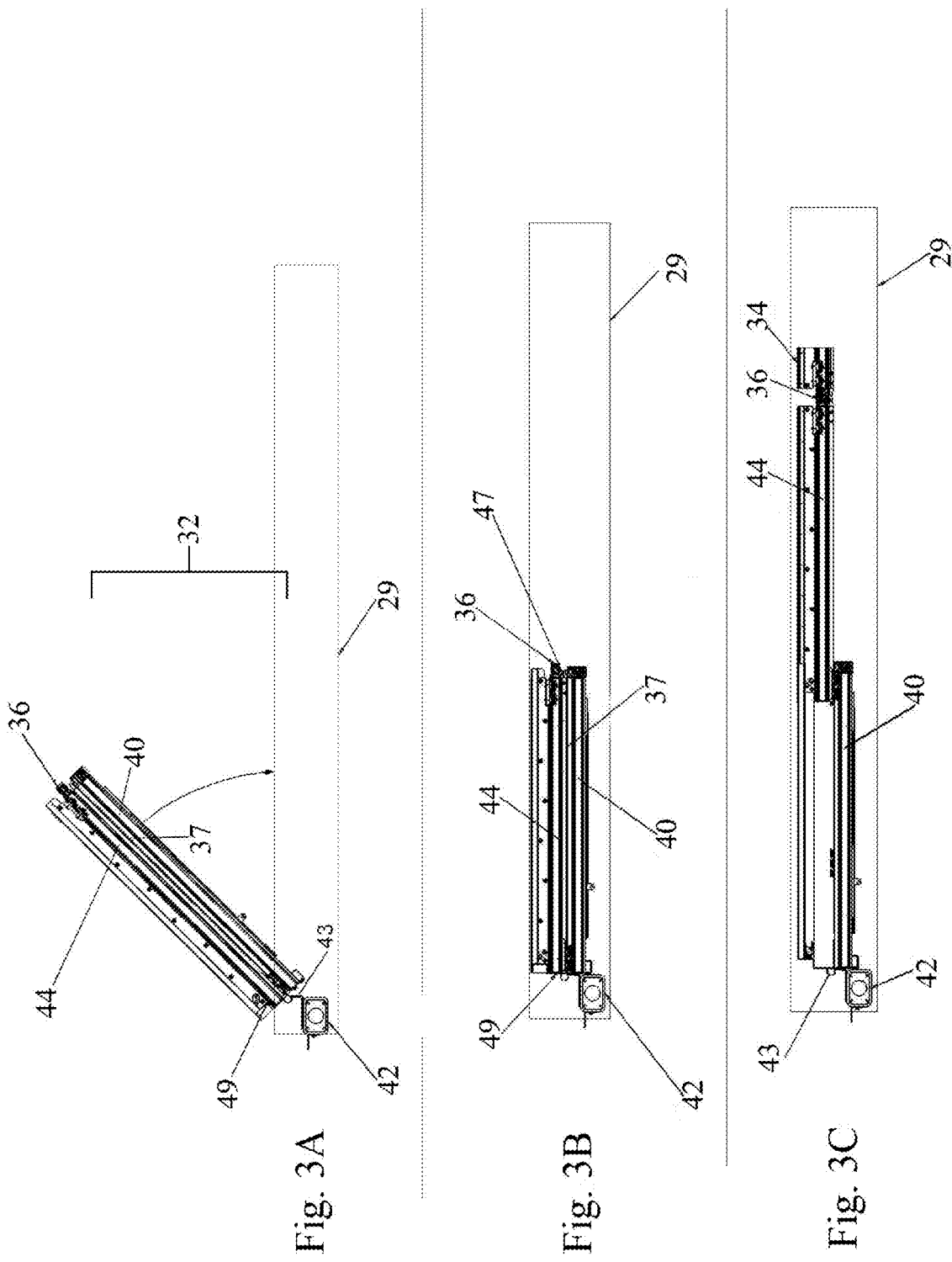

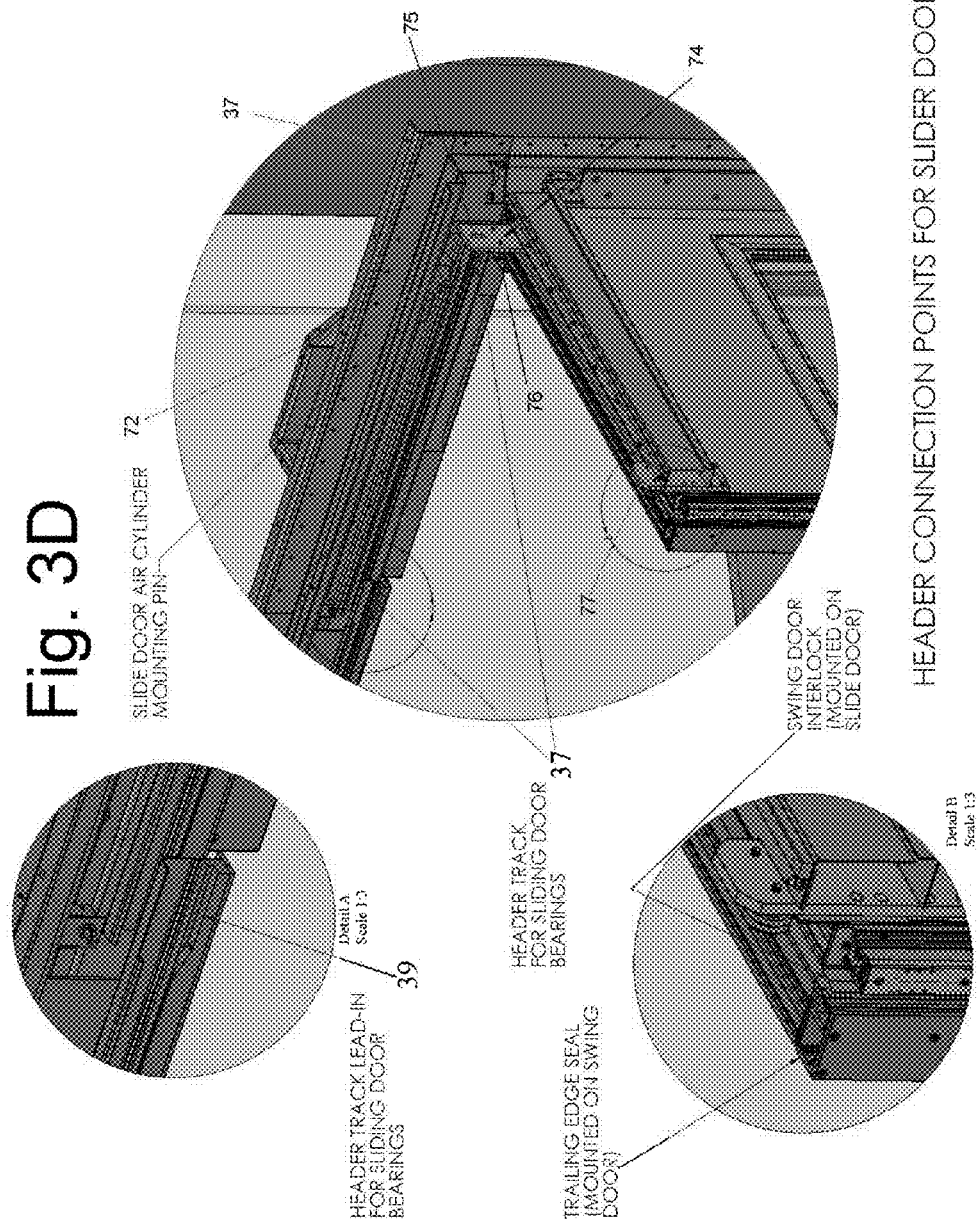

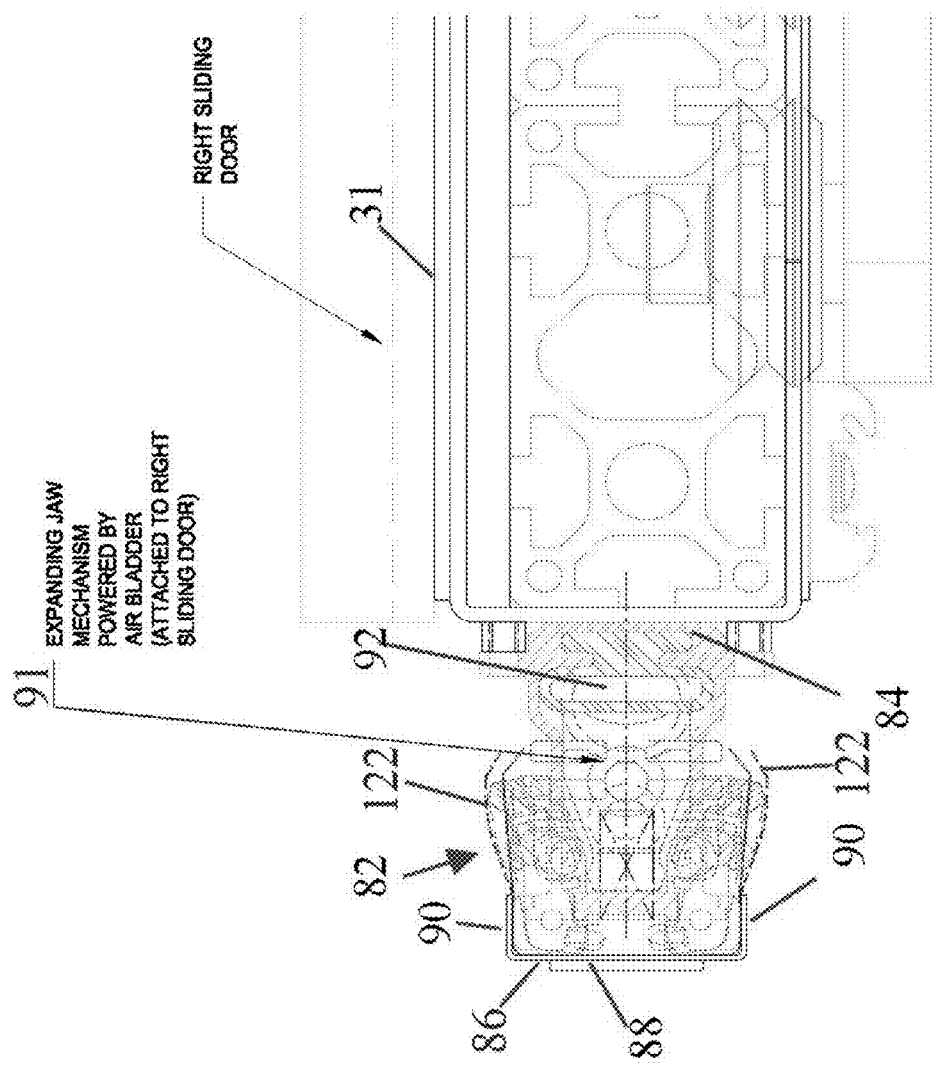

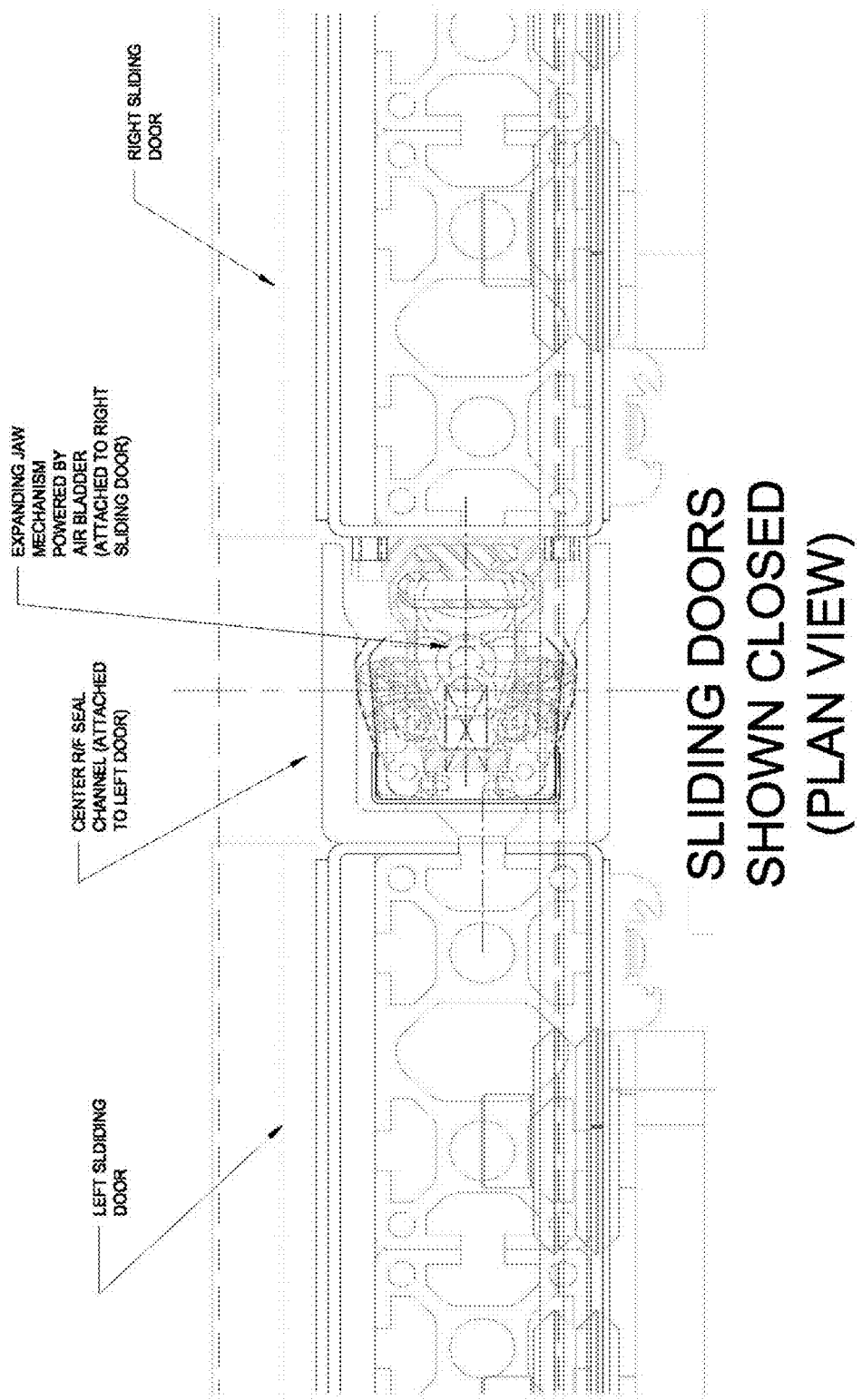

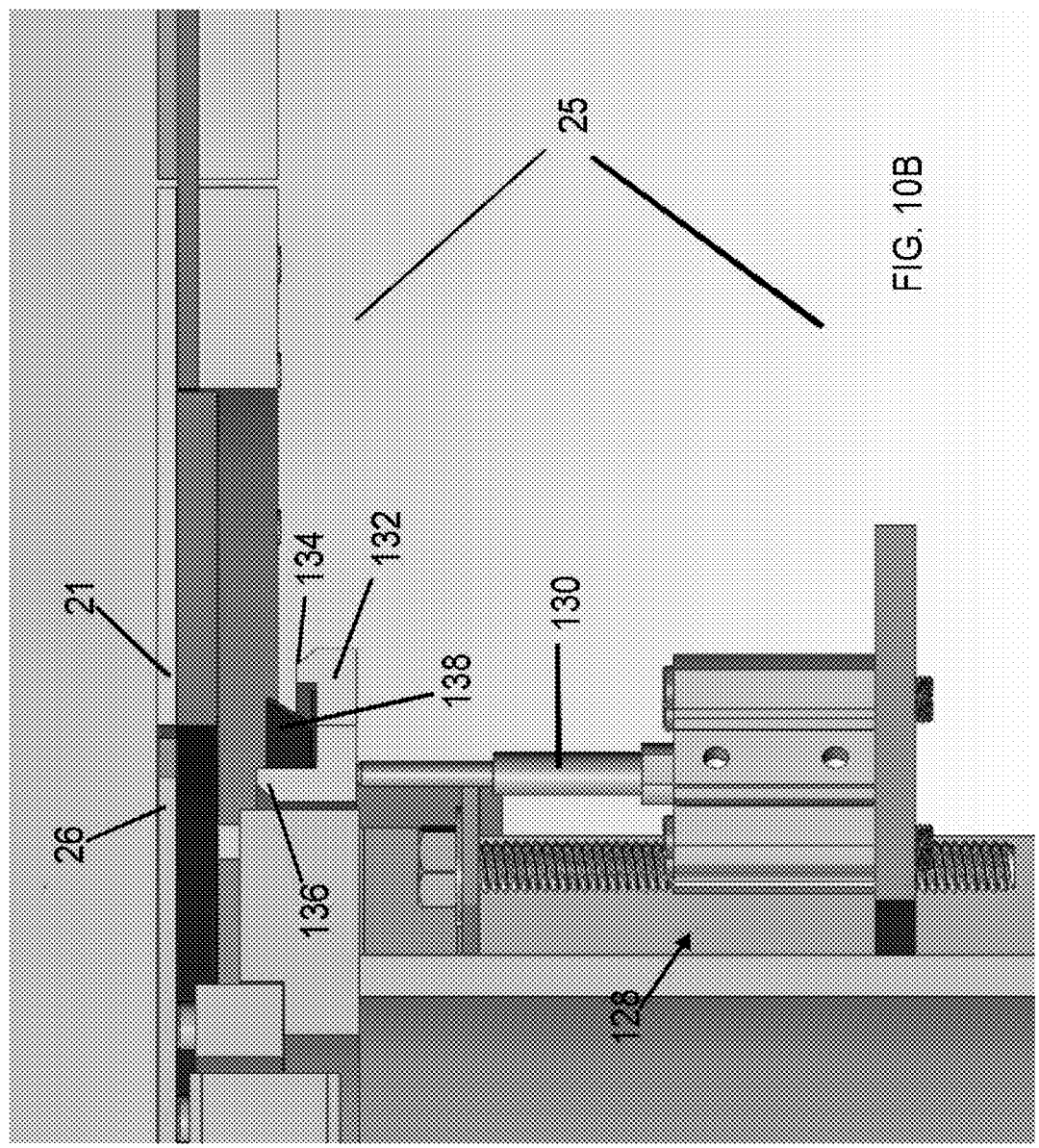

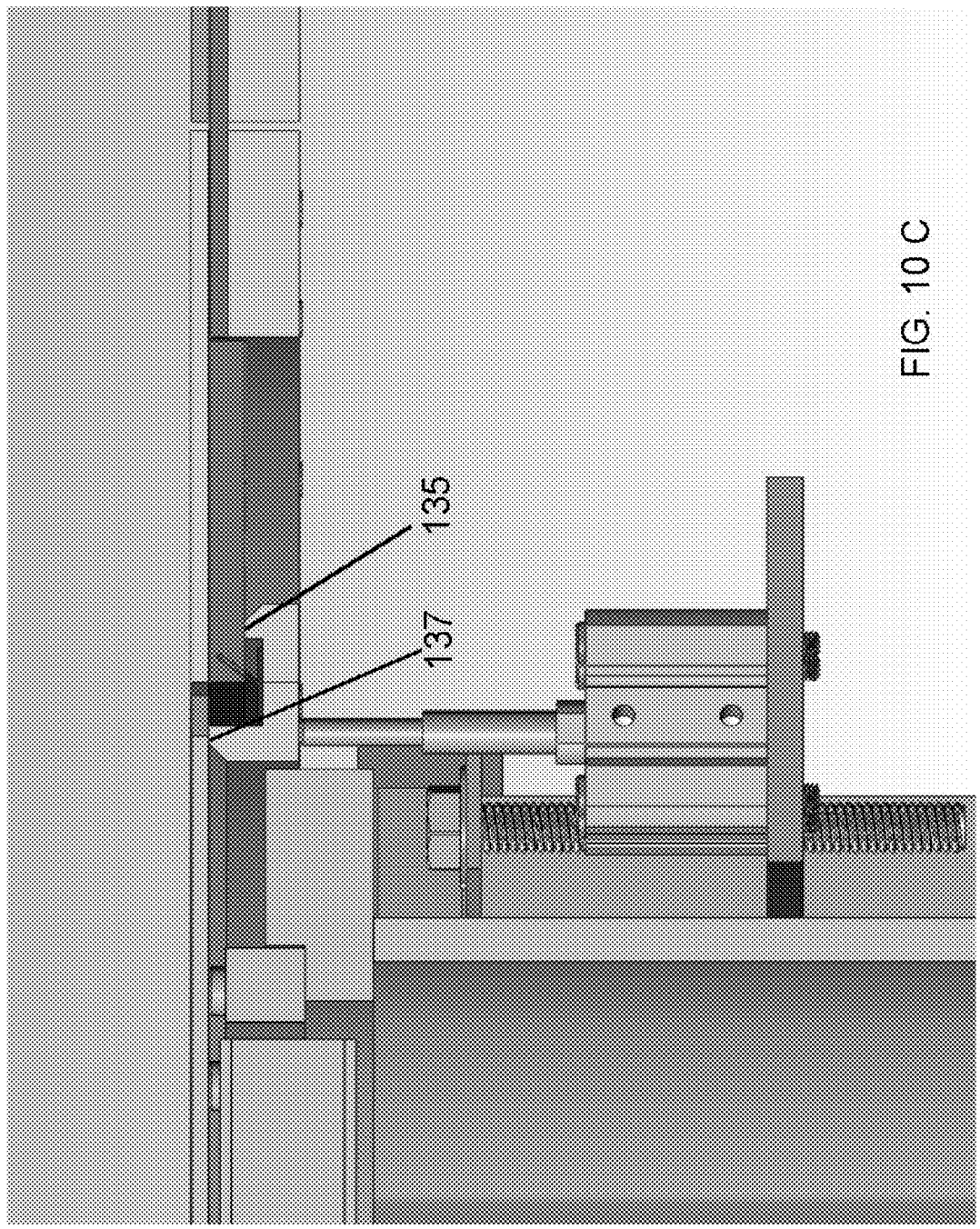

MOVABLE EMF SHIELD, METHOD FOR FACILITATING RAPID IMAGING AND TREATMENT OF PATIENT

PRIORITY

This U.S. Utility Patent Application claims the benefits of U.S. Provisional Patent Application No. 61/664,276 filed on Jun. 26, 2012.

BACKGROUND OF THE INVENTION

1. Field of the Invention

The present invention relates to Magnetic Resonance Imaging (MRI) and Linear Accelerator (LINAC) technologies, and more specifically, the present invention relates to a system for stowing and deploying MRI and LINAC equipment within the same enclosure for rapid patient imaging and treatment.

2. Background of the Invention

MRI is the de facto standard for soft tissue imaging. It allows physicians to know precisely the location of injury, tumor growth, and organ malfunction. This aids surgeons in pinpointing situs of entry into the body. It also facilitates non-invasive treatment, such as radiation therapy.

MRI has drawbacks related to non-invasive treatment scenarios. Structures (organs, tumors, fluids) within the body move, sometimes shifting by as much as an inch within a few minutes. So, an MRI image taken at minute 0 may be inaccurate at minute 3, particularly when the image is generated to determine the precise location of a neoplasm or tumor to be subjected to an externally-applied radiation beam from a LINAC or some other non-invasive treatment modality.

Ubiquitous electromagnetic radiation can cause artifacts and aberrations in MRI images. Unfortunately, every electronic device (including radiation treatment machines such as LINACs) emanates extraneous electromagnetic radiation (EMR), which while harmless to humans, wreaks havoc with MRI image quality.

Special rooms are therefore necessary to house MRI devices, these rooms designed to seal off any incursion of EMR. The problem becomes how an MRI imaged patient can be then quickly shuttled from the MRI enclosure to an area (albeit awash in EMR) for treatment by a LINAC or other electronic device. The LINAC cannot be housed in the same room as the MRI due to the LINAC emitting electromagnetic radiation. But, the organs in the body continually shift such that targeting and irradiating internal structures becomes problematic even just a few minutes after imaging.

State of the art solutions include enclosing an MRI machine in an EMI cladded room, but then having an adjoining room for radiation treatment.

A need exists in the art for an LINAC-MRI enclosure configuration which minimizes the time between patient imaging and patient radiation treatment. The configuration should accommodate conventional size LINAC and MRI equipment The configuration should also allow both pieces of equipment to co-exist in the same operating theatre while providing the necessary protection to, and from, each piece of equipment while it is in use. The configuration should also minimize patient movement during imaging, during patient transition from imaging to treatment, and during treatment.

SUMMARY OF INVENTION

An object of the invention is to provide an MRI/LINAC enclosure and configuration that overcomes many disadvantages of the prior art.

Another object of the invention is to provide a compact MRI/LINAC enclosure. A feature of the enclosure is the imposition of movable EMI shields between imaging and treating equipment. An advantage of the enclosure is that radiation treatment is enabled within 30-45 seconds after imaging of the patient has determined the situs of the tumor to be irradiated.

The invention provides a radio frequency shield which reversibly transects an electromagnetic frequency enclosure, the shield comprising a first plurality of panels attached to a first surface of the enclosure, wherein the first plurality is adapted to move through a first arc relative to the first surface, and also a first panel from said first plurality having a first leading edge capable of transecting the first arc; a second plurality of panels attached to a second surface of the enclosure, wherein the second plurality is adapted to move through an arc relative to the second surface of the enclosure, and also a second panel from said second plurality having a second leading edge capable of transecting the second arc so as to oppose the first leading edge; and a means for reversibly attaching the first leading edge to the second leading edge while simultaneously establishing electrical communication between the first and second plurality of panels.

Also provided is a device for establishing electrical communication between a plurality of leaves and a room enclosure, the device comprising a plurality of jaws mounted to a first opposing end of a first sliding door leaf; a receiving end adapted to receive the first opposing end, wherein the receiving end is mounted to a second opposing end of a second sliding door leaf; a cantilevered member in rotatable communication with the second opposing end; and a means for simultaneously contacting the jaws to the second sliding door leaf and extending the cantilevered member so as to establish an EMF shield between the leaves, above the leaves, and below the leaves.

BRIEF DESCRIPTION OF DRAWINGS

The invention together with the above and other objects and advantages will be best understood from the following detailed description of the preferred embodiment of the invention shown in the accompanying drawings, wherein:

FIG. 1 depicts a perspective view of an embodiment of the invented MRI-LINAC suite, with a removable EMI shield deployed, in accordance with features of the present invention;

FIG. 2 depicts a plan view of the invented MRI-LINAC suite, showing the removable EMI shield undeployed, in accordance with features of the present invention;

FIG. 3A depicts a plurality of EMF shield panels in an undeployed configuration, in accordance with features of the present invention;

FIG. 3B depicts a plurality of EMF shield panels in an undeployed, but track-nested configuration, in accordance with features of the present invention;

FIG. 3C depicts a fully deployed EMF shield, in accordance with features of the present invention;

FIG. 3D depicts another view of a plurality of EMF shield panels in undeployed configuration, with detail related to sliding door actuation, in accordance with features of the present invention;

FIG. 4B depicts coupling features of a second opposing door of a movable EMI shield prior to electric coupling with the first opposing door shown in FIG. 4A, in accordance with features of the present invention;

FIG. 4C depicts the coupling mechanism of the first opposing door of FIG. 4A in physical and electrical contact with the coupling mechanism of the second opposing door of FIG. 4B, in accordance with features of the present invention;

DETAILED DESCRIPTION OF THE INVENTION

Figure 4A:
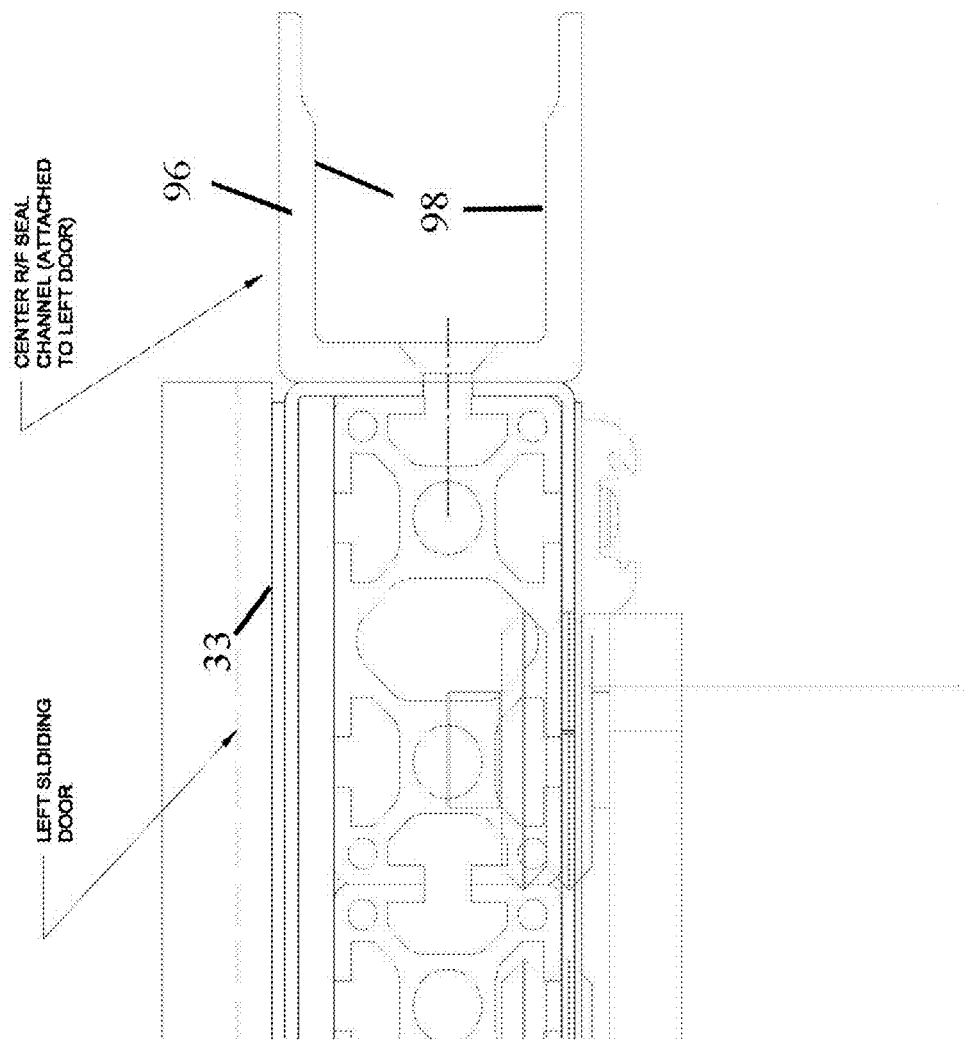
FIG. 4A depicts coupling features of a first opposing door of a movable EMI shield prior to electric coupling with a second opposing door, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a compact enclosure for both LINAC and MRI equipment. FIG. 1 depicts the enclosure, designated as numeral 10. Within the enclosure is situated a LINAC machine 12 and an MRI machine 14. Disposed intermediate the machines is a reversibly positioned EMI shield 16. The shield is depicted in FIG. 1 in a closed or fully deployed configuration.

Also within the confines of the enclosure 10 is a patient support surface 18. The surface 18 is depicted as parallel to a floor 20 of the enclosure. However, the surface is itself supported by a means 22 for pitching, yawing, and rotating the surface relative to the plane defined by the floor 20.

A depending end 24 of the support means 22 is in rotatable communication with a portion of the floor defining a carousel 26. FIG. 2 provides a plan view of the patient support surface 18 and underlying carousel 26. FIG. 2 depicts the EMI shield 16 in an open configuration.

FIG. 2 also shows the emission port 28 of the LINAC directed toward the floor, compared in FIG. 1 wherein the port 28 is shown pointed away from the floor. This change in emission port configuration is necessary to leverage the compact design of the enclosure 10. With its LINAC emission port on its side, the expanse of the LINAC machine is minimized to allow closure of the EMI removable shield 16. (The MRI deployed or closed-shielded configuration is depicted in FIG. 1.) In this deployed or closed-shield configuration, the MRI is electrically isolated and otherwise shielded from electromagnetic radiation emanating from the always on LINAC.

After patient imaging, the removable shield 16 is opened and the patient support surface 18 is moved to align with the LINAC emission port 28. The short distance between the MRI and LINAC machines, enabled by the configuration of the removable shield 16, allows patient surface alignment in less than a minute.

Door Detail

A salient feature of the enclosure is the utilization of the EMI shield 16 removably positioned between the LINAC and MRI equipment. As depicted in FIG. 1, the shield comprises a first plurality 30 of panels and a second plurality 32 of panels, wherein the first plurality defines a first leading edge 34, the second plurality defines a second leading edge 36 and the edges are in slidable opposition to each other.

Each of the first plurality of panels and second plurality of panels comprises two panels and said two panels are in slidable communication with each other. FIG. 3A-C depicts the second plurality of panels 32. The second plurality 32 is first depicted (FIG. 3A) outside a door header 29, and in pivotal relation thereto. The header 29 is rigidly attached to the ceiling of the enclosure. A first panel 40 is pivotally mounted to a first door jamb 42 of the enclosure via a hinge 43, such as a continuous hinge similar to a piano hinge. In an embodiment of the invention, the swing door is secured to the frame jamb legs by a continuous hinge. A second panel 44 is mounted to the first panel so as to be in slidable communication with the first panel.

In operation, the plurality of panels 32 is rotated (in the direction of the arrow) from un-deployed configuration, that rotation occurring about the hinge 43. In an embodiment of the invention, the hinge used resembles a piano hinge, the hinge 43 extending vertically from the header to the threshold of the jamb and positioned between tracks 37. The tracks 37 are slidably engaged by the second panel 44 whence the plurality of panels 32 is swung within the header.

FIG. 3B depicts the plurality of panels 32 substantially nested within the header 29. The direction of rotation is depicted in dashed arrow lines seen in FIG. 2 and in 3A.

After the aforementioned pivoting action, the second panel 44 is extended in a distal direction (FIG. 3C) such that its second leading edge 36 engages with the first leading edge 34 of the first plurality 30 of panels, similarly deployed along the same door header 29 . With the two pluralities (30, 32) of panels so deployed, the enclosure is transected by the panels such that an EMF shield is created to electrically isolate the LINAC from the MRI equipment.

One fully deployed, an embodiment of the door configuration features the opposing edges 34, 36 of the first plurality of panels 30 and the second plurality of panels 32 being maintained in intimate electrical contact. An embodiment for establishing this electrical contact comprises an air pressure-actuated bladder backstopping a flexible conductive metal strip. An exemplary bladder-actuated mechanism is disclosed in U.S. Pat. No. 5,569,878, the entirety of which is incorporated herein by reference.

FIG. 3D provides detail of the sliding door actuation system. An embodiment of the sliding door (second panel 44) actuation system comprises a rod-less air cylinder which is in slidable communication with the door header 29 attached to the ceiling of the enclosure. A portion of the air cylinder defines a pin 72 extending toward the panels when the panels are in their nested configuration as depicted in FIG. 3B. Opposing the pin 72 in this nesting configuration is a first sliding door hanger 74 having a first end and a second end, whereby the first end is positioned superior to the second end. The first sliding door hanger 74 is rigidly affixed to a distal top peripheral region of the sliding panel (second panel 44). A region of the first end of the first sliding door hanger 74 defines an aperture 75 adapted to receive the pin 72 when the plurality of panels are in the nesting position in the track 29, as depicted in FIG. 3B. Upon actuation of the piston-less air cylinder, the pin travels toward the leading or distal end of the panels, thereby causing the sliding door (second panel 44) to move in a distal direction.

The second end of the first sliding door hanger 74 is in rotatable communication with a first roller 76 such that the axle of the roller is affixed to and extends transversely through the second end. A second sliding door hanger, 77, is affixed to a distal end of the sliding door, and contains a second roller, similarly mounted. The track 37 is configured as U (i.e., a horizontally disposed substrate flanked by two upwardly extending legs). The top of the track defines a cross section adapted to slidably receive the first and second rollers. A portion of the upwardly extending leg of the U proximal to the sliding panel 44 defines a cut out 39 so as to facilitate initial engagement of the rollers with the beginning of the track. The overhead rollers that support the slide door panel while engaged with the header tracks (i.e. second hanger) 77 are positioned diagonally from each other as a means to stabilize the sliding door and prevent the bottom of the sliding door from swinging away from a dead center position, i.e., a position in close spatial relationship with the swinging door (the first panel 40), as depicted in FIG. 3B.

Figure 5A:
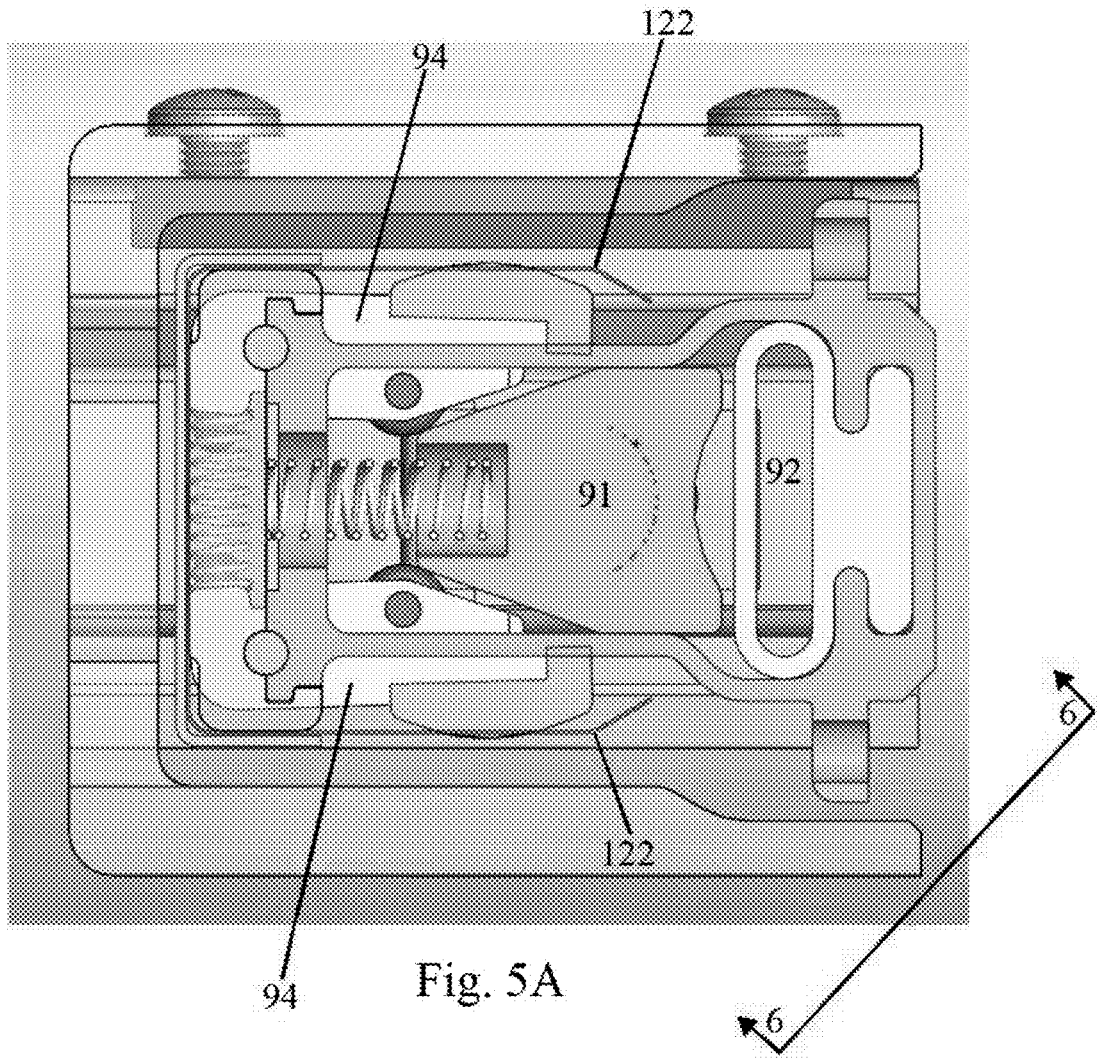
FIG. 5A is a detailed view of two physically nested coupling mechanism not in electrical communication with each other, in accordance with features of the present invention.

Another sealing embodiment comprises a reversibly expandable bladder that actuates a series of laterally extending rollers positioned along substantially the full length of a medially facing surface of one or both vertical edges of a door. FIGS. 4A-C illustrate this sealing embodiment. In this embodiment, a first sliding leaf 31 of the first plurality of panels supports an expanding jaw mechanism 82. A proximal end 84 of the mechanism is attached to the first leading edge of the first sliding leaf 31. A distal end 86 of the mechanism 82 terminates in an electrically conductive cap 88. Axially extending regions 90 of the cap define channels which are adapted to receive laterally extending jaws 94 (as seen in FIG. 5A). In an embodiment of the invention, the channels extend horizontally. The jaws 94 are pivotally mounted to an interior surface of the distal end 86 of the mechanism. The jaws are medially biased when undeployed but actuated laterally via a pneumatically actuated bladder 92 which extends a frusto conically-shaped body 91 in contact with inwardly facing surfaces of a proximal end of the jaws.

The cross section of the expanding jaw mechanism 82 is complementary to a receiving end protruding from a second leading edge of a second sliding leaf 33. This receiving end 96 is adapted to slidably receive the expanding jaw mechanism 82. This engagement of the two leaves is depicted in FIG. 4C. The cross section of the receiving end 96 (FIG. 4A) is so dimensioned such that when a lateral force is applied to the jaws, the jaws contact an inside surface 98 of the receiving end with a force sufficient to keep the first sliding leaf from inadvertently disengaging from the second sliding leaf. In this configuration, the first sliding leaf 31 and second sliding leaf 33 are in electrical communication with each other. As such, the jaws so deployed serve as a means for both physical locking the opposing leaves together and also establishing electrical communication between the leaves.

FIG. 5A is a detailed view of the jaw mechanism 82 nested within the receiving end 96. In this configuration, the jaws 94 are shown in an un-deployed configuration, their proximal ends 104 pivotally mounted to the distal end 86 of the jaw mechanism. A laterally biased spring 95 engages or otherwise contacts the proximal ends 104 of the jaws, so as to bias the proximal ends of the jaws similarly laterally. This provides a medially directed bias to the distal ends of the jaws. The bladder is also shown un-deployed (i.e., deflated).

Figure 5B:
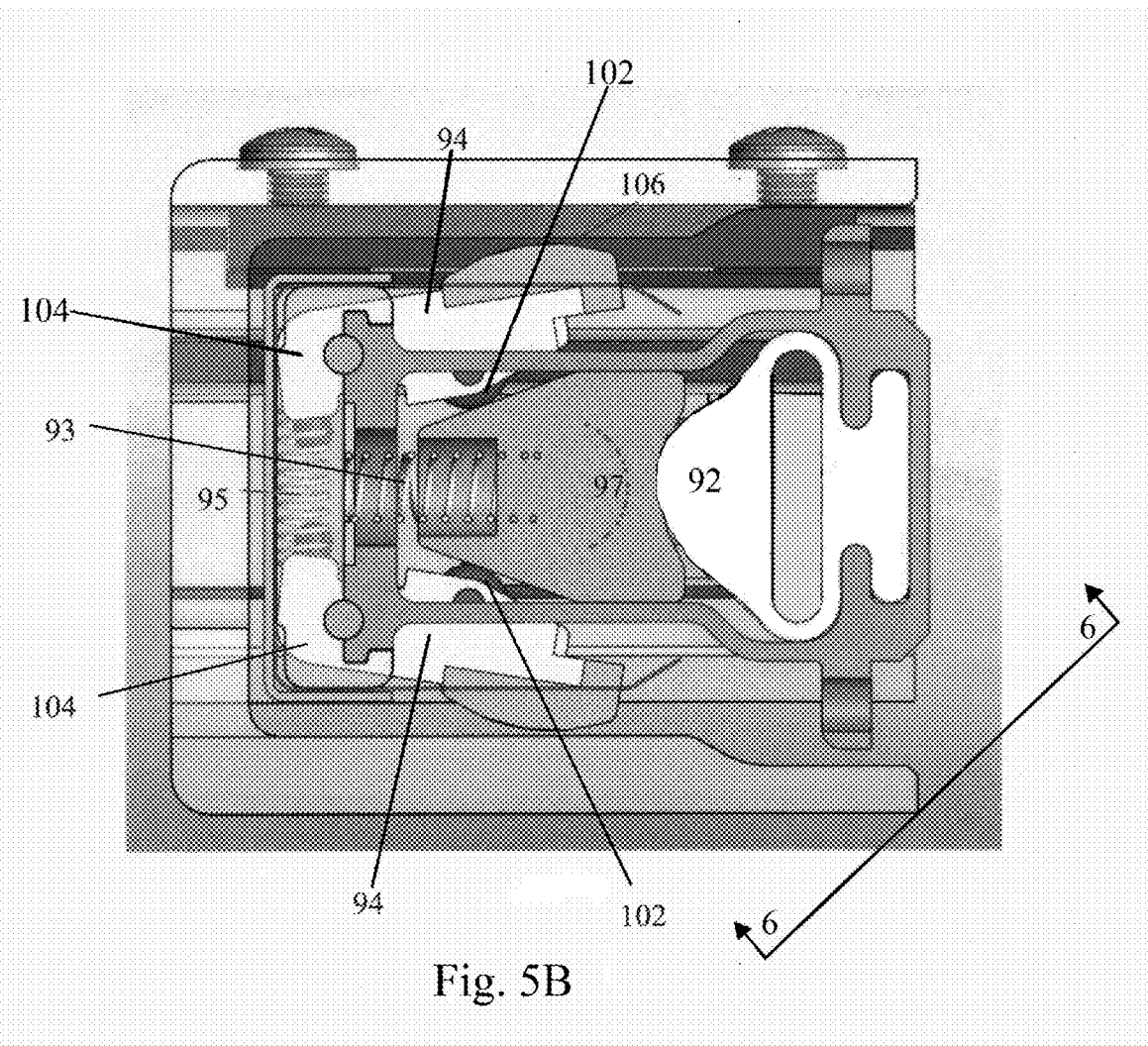
FIG. 5B is a detailed view of two physically nested coupling mechanism also in electrical communication with each other, in accordance with features of the present invention.

FIG. 5B is a detailed view of the jaw mechanism 82 nested within the receiving end 96 but with the jaws deployed laterally. The bladder 92 is also seen deployed.

In operation, the bladder 92, once pneumatically actuated, extends axially to contact a proximal end 100 of a slidably disposed, frusto-conically shaped first cam body 96. Upon contact with the bladder 92, the first cam body 97 slides axially within the expanding jaw mechanism 82 and away from the bladder such that it extends in a direction parallel to the plane formed by the engaged first and or second sliding leafs.

A plurality of rollers 102, rotatably mounted to the jaws, contact the frusto-first cam body as the first cam body 97 is urged axially by the expanding bladder. This action causes distal, laterally facing surfaces 106 of the jaws to contact with the medially facing surfaces 98 of the receiving end 96. In an un-deployed configuration, the first cam body 97 is biased toward the first leading edge of the first sliding leaf via an axially disposed spring.

In an embodiment of the invention, electrically conductive strips 122 are positioned between the jaws 94 and the medially facing surfaces 98 of the receiving end 96 of the second door leaf. A first end of each of the strips are in electrical communication with the axially extending regions 90 of the electrically conductive cap 88 forming the terminus of the distal end 86 of the sealing mechanism mounted to the first leaf. Specifically, a proximal end of the strip is attached to the cap, while a distal end is left free hanging or otherwise unattached. Upon outward deflection by the jaws, the strips are concomitantly urged laterally to contact the medially facing surfaces, thereby establishing electrical communication between the first leaf and the second leaf.

Aside from the aforesaid rollers and air pressure-actuated bladders, other edge deployment mechanisms include a vertically-extending bar which is laterally actuated to impose pressure along the length of the underside of a similarly disposed, vertically-extending electrically-conductive strip.

When the opposing edges are aligned along line β-β (which said line is collinear with the door header 29), such that the sliding leaves define a continuous plane, the bladder is pressurized or otherwise deployed to activate the expanding elements. A substantially complete EMI seal is therefore established simultaneous with a firm locking together of the opposing panels to avoid inadvertent opening.

Figure 6A:
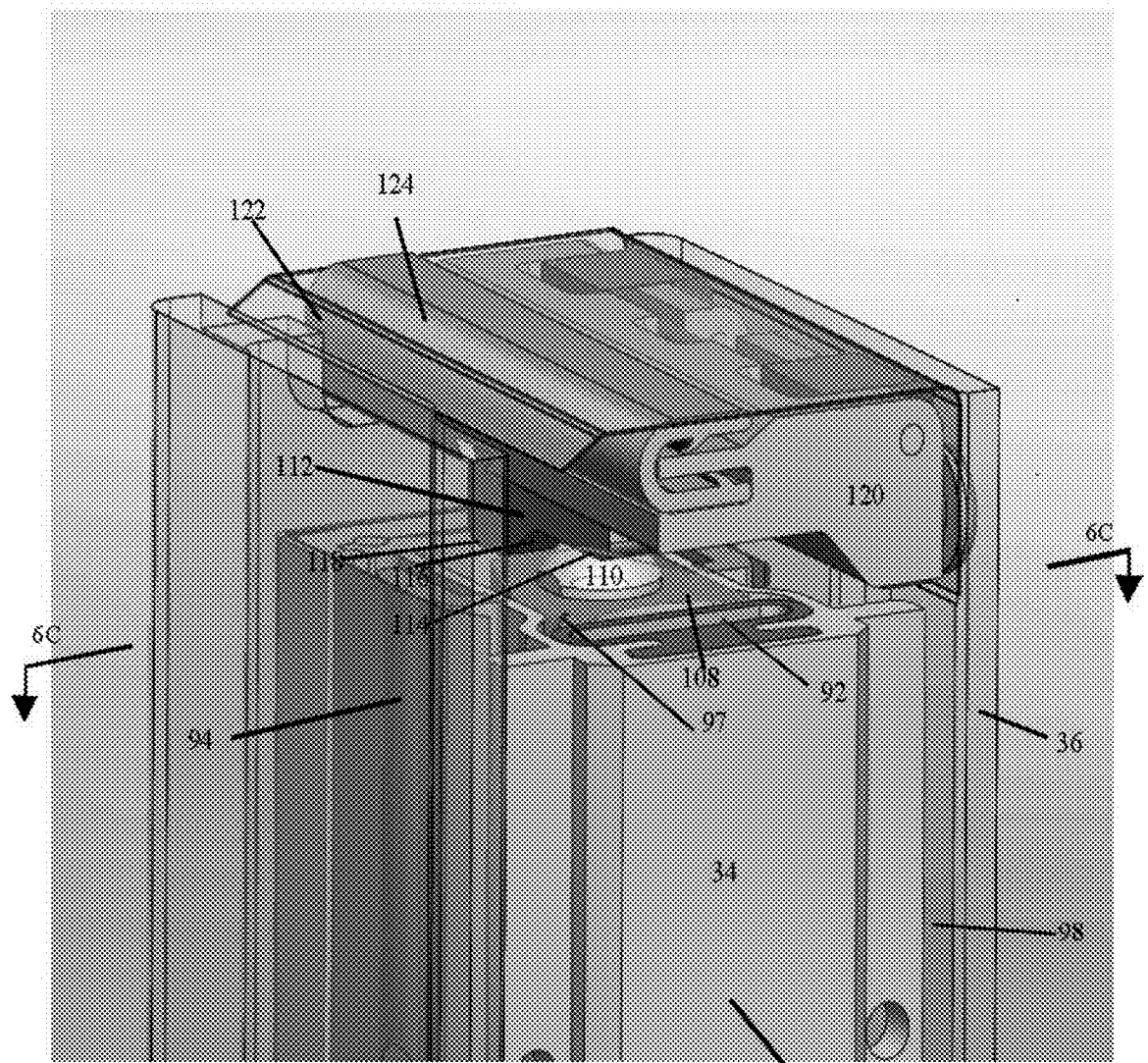
FIG. 6A is a view of FIG. 5A taken along line 6-6.
Figure 6B:
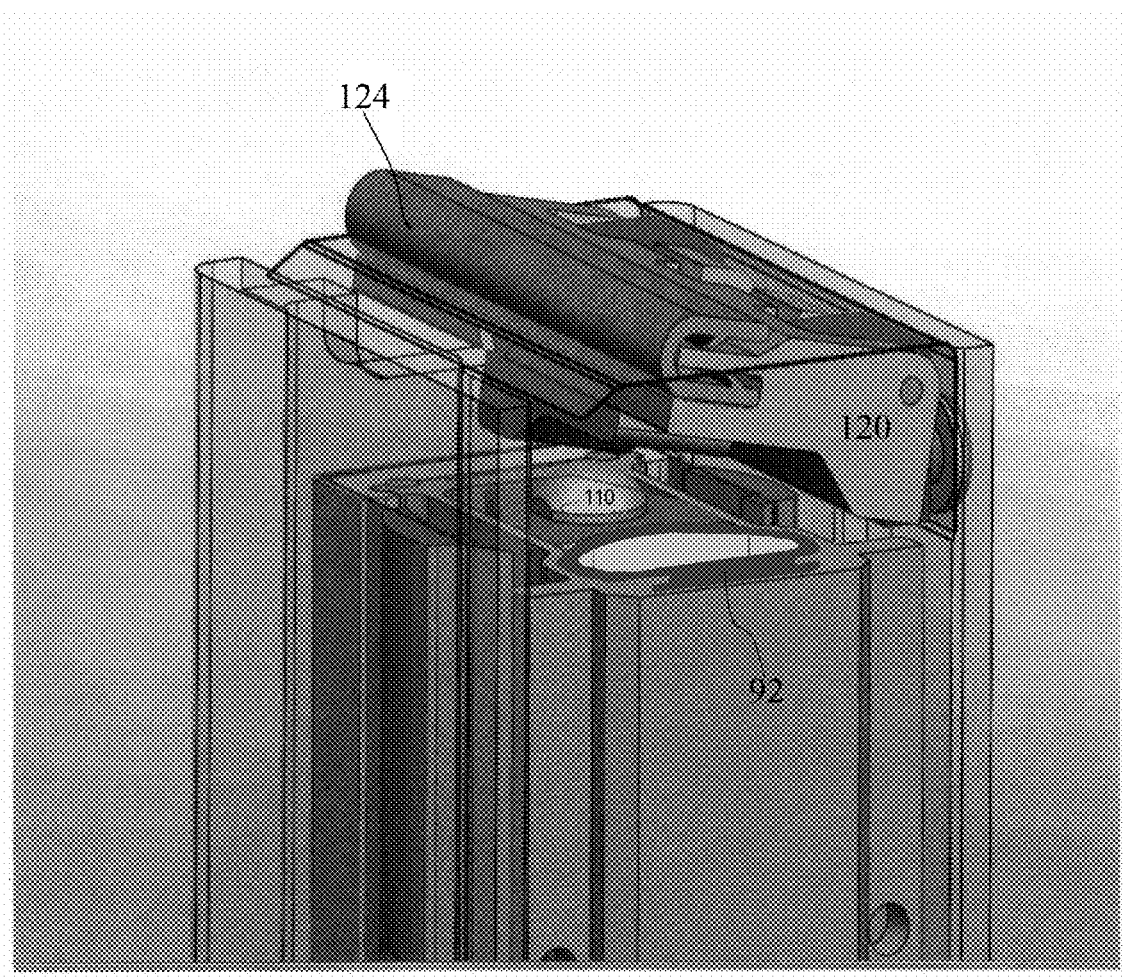
FIG. 6B is a view of FIG. 5B taken along line 6-6.

Directly above and below the line formed by the abutting sliding door leaves (i.e., along the ceiling and floors of the enclosure directly opposing the top and bottom edges of the leaves), an additional means is employed to seal EMI gaps. This means is depicted in FIGS. 6A and 6B. Both figures show the first leading edge 34 of the first sliding leaf nested within the second leading edge 36 of the second sliding leaf. As in FIG. 5A, FIG. 6A shows the sealing means in an un-deployed configuration, wherein the bladder 92 is deflated. In this configuration, the first cam body 97 is in its resting position such that the jaws 94 are not laterally extending. With the jaws so retracted, the first sliding leaf 31 and the second sliding leaf 33 are not yet locked together.

The first cam body 97 as depicted in FIG. 6A defines an upwardly facing surface 108. Approximately centrally located upon the surface 108 is a protuberance 110 in the approximate shape of a half sphere, such that the protuberance is convex in topography. In an embodiment of the invention, distal regions of the surface 108 define an incline such that the surface extends at an upslope from the region of the surface in close proximity to the bladder.

Directly opposing the protuberance 110 is a second cam body 112 configured as an upside down step. Therefore, the second cam body defines a first, downwardly facing surface 114, a second surface 116 disposed at an angle to the first surface 114, and a third surface 118, also defining a downwardly facing surface. This third surface resides on a plane that is beneath or lower than the plane on which the first surface 114 resides. The second surface is disposed between the first and third surface and forms a continuous surface with the first and third surface. The cam body 112 could also define a continuous slope, i.e., with a discrete step.

The second cam body 112 is rigidly attached to a cantilevered member, hereinafter referred to as a swing member 120, itself rotatably attached at its proximal end to a superior region of the second leading edge of the second sliding door leaf. The superior region is in close spatial relationship with the door header 29 so as to facilitate intimate electrical contact between the panel and the track, as discussed infra.

The protuberance 110, when the bladder is not inflated (as depicted in FIG. 6A), directly opposes the first surface 114 of the second cam body. However, when the bladder is inflated (see FIG. 6B), the first cam body protrudes axially, the protuberance contacts the second surface 116 and comes to rest against the third surface 118. This axial movement by the first cam body causes its protuberance to slide along the second cam body from the first cam surface 114 through the second cam surface 116, and finally stopping on the third cam surface 118. This action results in the second cam surface moving in a vertical direction relative to the first cam surface. This action therefore results in the swing body 120 extending beyond the horizontally disposed periphery of the door leaf, such that the swing body extends vertically.

Figure 6C:
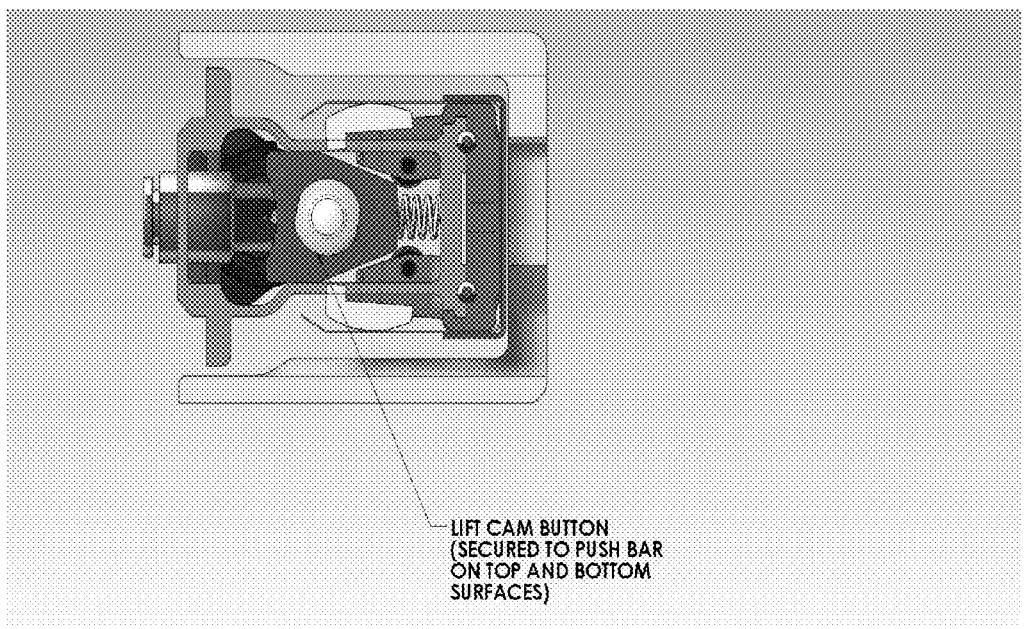
FIG. 6C is a view of FIG. 6A taken along line 6C-6C.

FIG. 6C is a view of FIG. 6A, taken along line 6C-6C. As depicted, the camming mechanism is encapsulated by a vertically extended housing 35, which defines a first laterally facing surface (i.e., the first leading edge 34) of the leaf. The first cam body 97 is biased outwardly toward the first leading edge 34, i.e., toward the periphery of the door leaf. This biasing is effected by a pressure inducement means such as a spring 124 positioned intermediate a distally facing surface 126 of the first cam surface 97, and a second laterally facing surface 38 of the vertically extended housing 35. The spring 124 is disposed generally horizontally so as to provide a means for urging the cam surface 97 outwardly (toward the leading edge of the leaf) to an undeployed position.

In operation, rotation of the swing member occurs through an arc from a position perpendicular to the plane formed by the engaged first and second leaves, to a final position that is parallel to the plane. Specifically, at rest, when the bladder is not deflated, the swing member is positioned perpendicular to the aforesaid plane. When the bladder is inflated, the swing member is deployed along an arc which is defined at one end by the resting position of the swing member, to a position of the swing member being parallel to the plane formed by the engaged door leaves. However, it should be appreciated that the swing member will extend along the arc only as far as necessary to contact an electrically conductive substrate which is attached to the enclosure. The electrically conductive substrate can be part of a horizontally disposed member of a door jamb positioned above and/or below the adjoining door leaves. In summary, the EMF shield is established above and below the adjoining door leaves simultaneous with the door leaves being locked together via action of the laterally extending jaws 94.

The remaining upper and lower door surfaces, i.e., the edges of the doors opposing the ceiling and the floor of the enclosure, will utilize reversibly expandable air bladders that push R/F metal sealing strips against the upper door beam and lower threshold surfaces, such as what is disclosed in U.S. Pat. No. 5,569,878, owned by the instant Assignee and incorporated in its entirety by reference.

Figure 7:
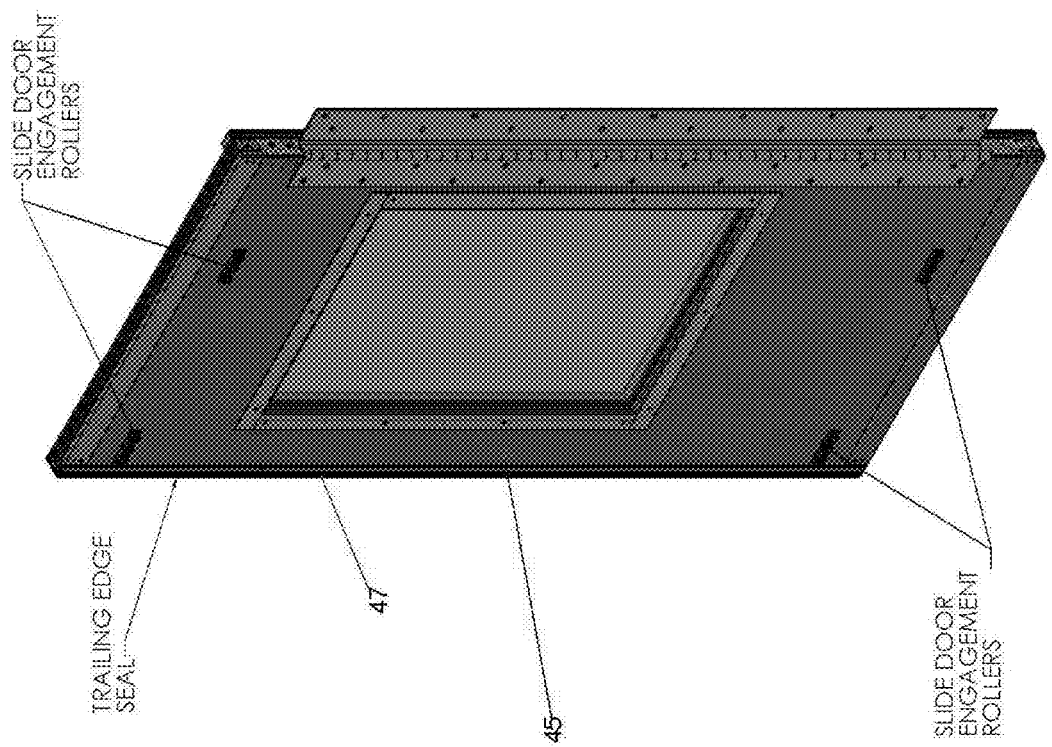
FIG. 7 is a perspective view of a swinging component of an emf shield, in accordance with features of the present invention.
Figure 8:
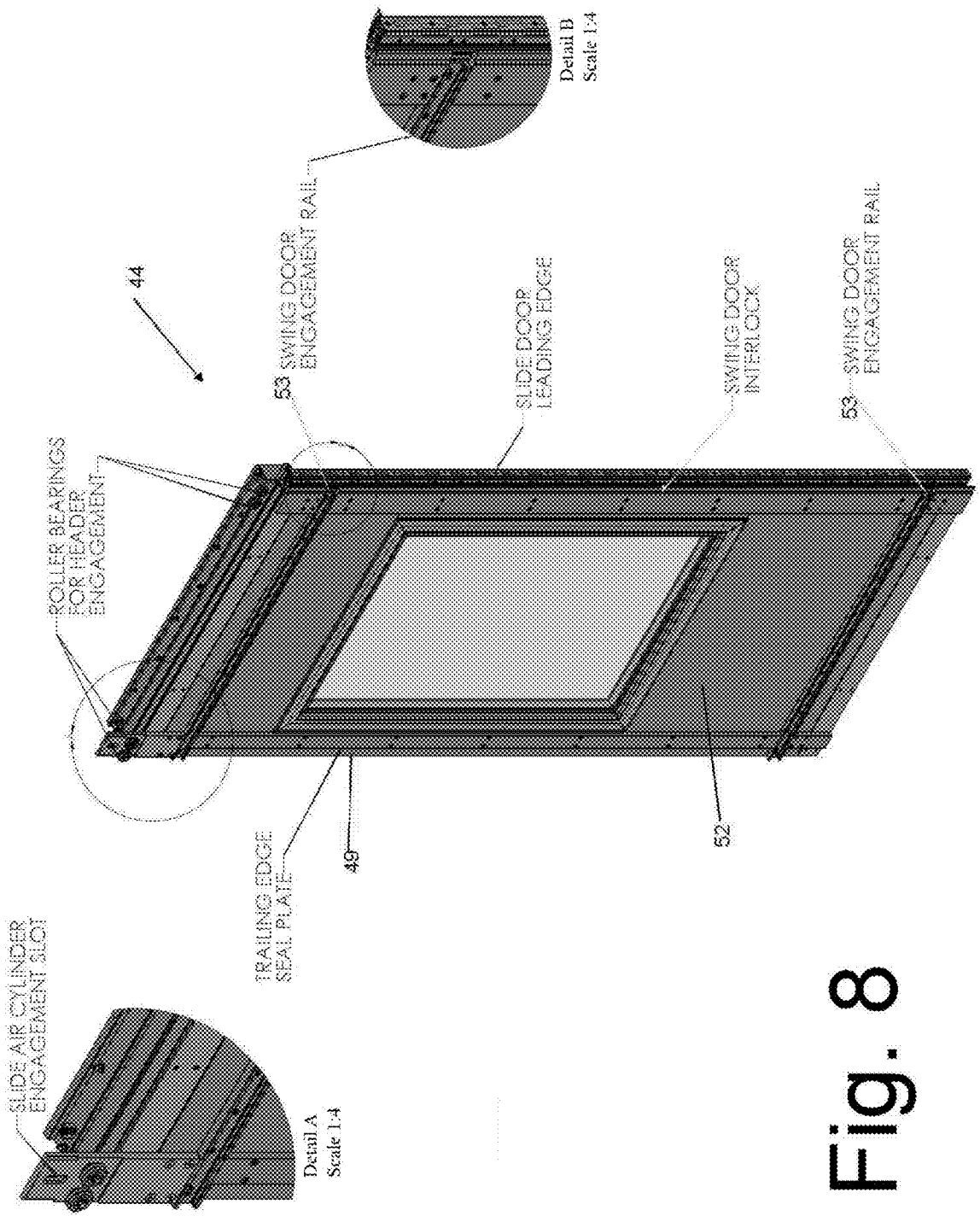
FIG. 8 is a perspective view of a sliding component of an emf shield, in accordance with features of the present invention.

To facilitate an EMF seal between the panels in each of the plurality of panels, opposing surfaces of the panels feature an edge seal in mating relation with an edge seal plate. Specifically, and as depicted in FIG. 7, a region of the medially facing exterior surface 45 of the first panel 40 defines an edge seal 47. This edge seal extends substantially the entire height of the panel from the top of the panel to the bottom of the panel. As depicted in FIG. 8, the second panel 44 defines an edge seal plate 49. The edge seal 47 is adapted to receive the edge seal plate 49 when the second panel 44 is slid outwardly to its most distal position in contacting the first leading edge 34 of the opposing sliding door of the first plurality of panels 30.

FIGS. 7 and 8 also depict sliding door engagement rollers 51 horizontally disposed along the medially facing surface 45 of the first panel 40 and swing door engagement rails 53 horizontally disposed along the medially facing surface 52 of the second (i.e., sliding) panel 44 to further facilitate alignment. The rails 53 are adapted to receive the rollers 51 so as to maintain a space between the panels during full deployment of the second panel 44 (i.e., the sliding door) from the first panel 40 (i.e., the swinging door. The rails 53 interact with the rollers while the swing door and the sliding door are coupled together, (i.e., when the two doors are positioned from outside to underneath the header 29 and also before the sliding door is slid away from the swing door). The rail 53/roller 51 interaction provides a means for keeping the doors together until the doors are slid apart to full deployment of the shield. As the sliding door partially disengages from the swing door, the sliding door's overhead rollers engage with the sliding door track 37.

EXAMPLE 1

In an embodiment of the movable emf shield, a sliding door (second panel 44) connects to the swing door (first panel 40) via two engagement rails 53 which are mounted on the upper and lower medially facing surface 45 of the sliding door. In an embodiment of the invention, the sliding door (panel 44) is always connected to the swing door (first panel 40) even when the swing door is not underneath the header 29. The swing door has corresponding roller bearings 51 that are positioned to be received by the rails when the swinging door panel is positioned within the track 29.

The header tracks (i.e., those tracks superiorly positioned relative to other tracks on the swinging door) are notched to allow the sliding door roller bearing to engage/disengage from the header. A rail cover on the header track prevents the sliding door from accidently disengaging from the track once the sliding door starts moving in a distal direction to engage with the opposing sliding door from the other plurality of panels (i.e., starts to deploy).

As discussed supra, the movable emf shield comprises one or more plurality of panels. When each of said plurality is in an un-deployed position (i.e. residing outside of the door header), the sliding door component (e.g., the second panel 44) is secured to the swinging door component (e.g. the first panel 40) via the upper and lower rails. The trailing edge seal 47 provides additional means to secure the sliding door to the swinging door, whereby the seal engages with the edge seal plate 49. This engagement, which may comprise a tongue and groove configuration, prevents the sliding door from shifting relative to the swinging door component.

Figure 9:
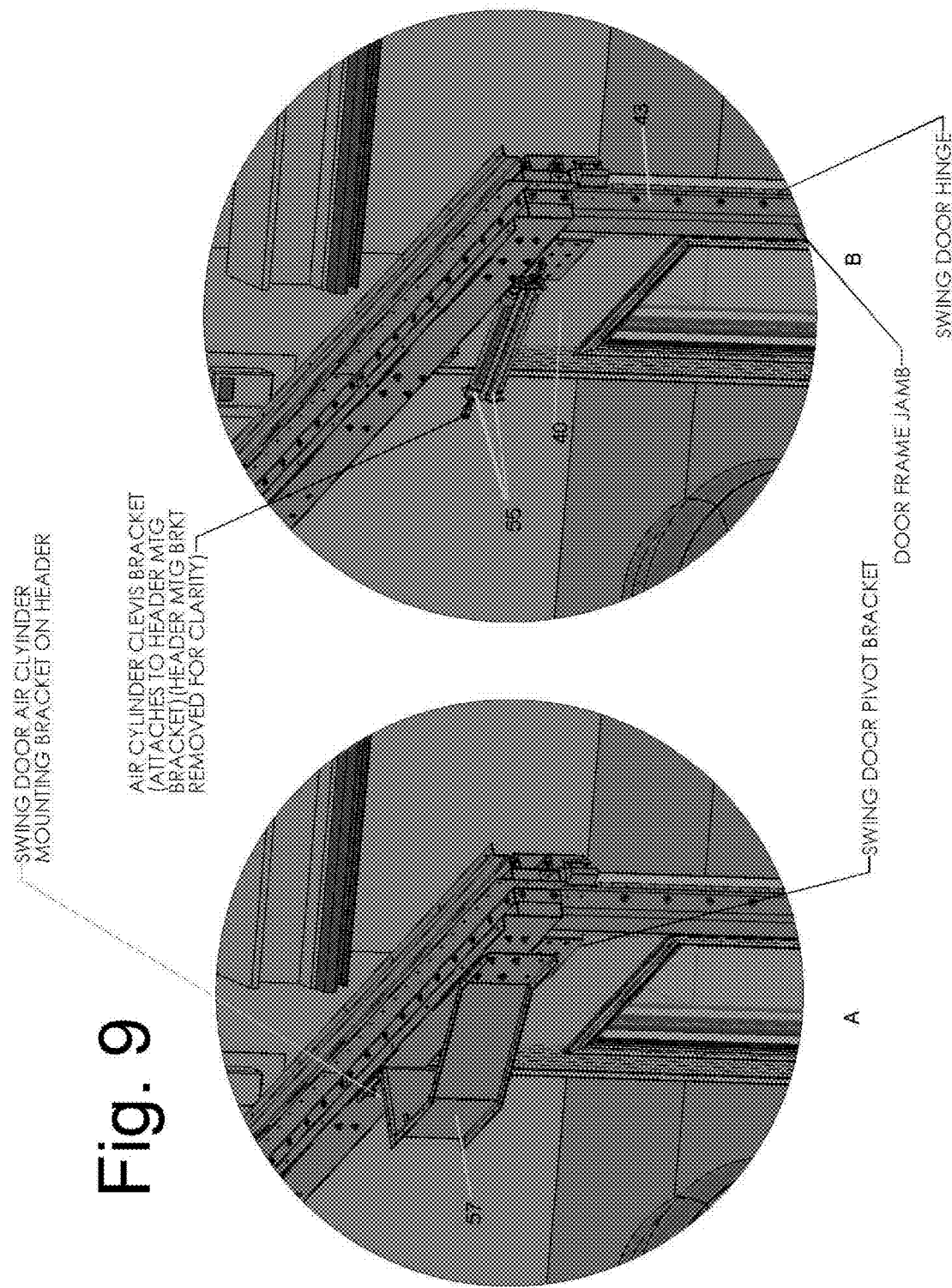
FIG. 9A-B are perspective views of a means for positioning a plurality of doors within a track, in accordance with features of the present invention.

When the plurality of doors swing from the un-deployed (FIG. 3A) to the deployed position (FIG. 3B), a means for finally positioning the plurality within the track 29 is utilized. One such means is the user's hand, foot or body whereby the user applies medial pressure to the outwardly facing surface of the swing door. Another means for setting the plurality of panels in the door header is depicted in FIGS. 9A-B. With this configuration, a plurality of air cylinders 55 compress, thereby urging the swing door to pivot on its hinge 43 until it is set or homed into position. In an embodiment of the invention a first end of one cylinder is attached to a header mounting bracket 57 secured to a ceiling region of the enclosure while a second end is attached to the outwardly facing surface of the swing door. A second cylinder is positioned adjacent to the first cylinder, such that a second end of the second cylinder is attached to a header mounting bracket while a first end of the second end of the second cylinder is attached to the outwardly facing surface of the swing door. With the two cylinders so arranged, the cylinders extend in opposite direction. This two-cylinder arrangement effectively doubles the extension, closing distances that a single cylinder arrangement would otherwise provide.

The opposite side of the door is secured to the frame header by means of an opposing air cylinder bracket. When the doors need to be opened (i.e. removed from underneath the header 29, the reverse facing air cylinders extend, causing the doors to swing open. The air cylinders are sized to allow the door to swing open only to a designed stop point.

When the doors need to be closed, (and therefore positioned underneath the header 29), the opposing air cylinders compress (i.e., retract) causing the doors to swing closed.

Due to the doors being connected through the rail and bearing system, when the swing door reaches its "home" position, the slide door header bearings reach the header track at the same time. A slide door air cylinder pin 72 (located in the header) nests within a corresponding engagement slot 75 on the door.

When the slide door is pushed along the header rails, the slide door disengages itself from the swing door roller bearings.

Carousel
Detail

A turntable is used to rotate, tip and otherwise position a patient support surface. Several turn tables are available commercially, including the LINAC turntable manufactured by Varian Medical Systems, Inc., Palo Alto, Calif.

Figure 10:
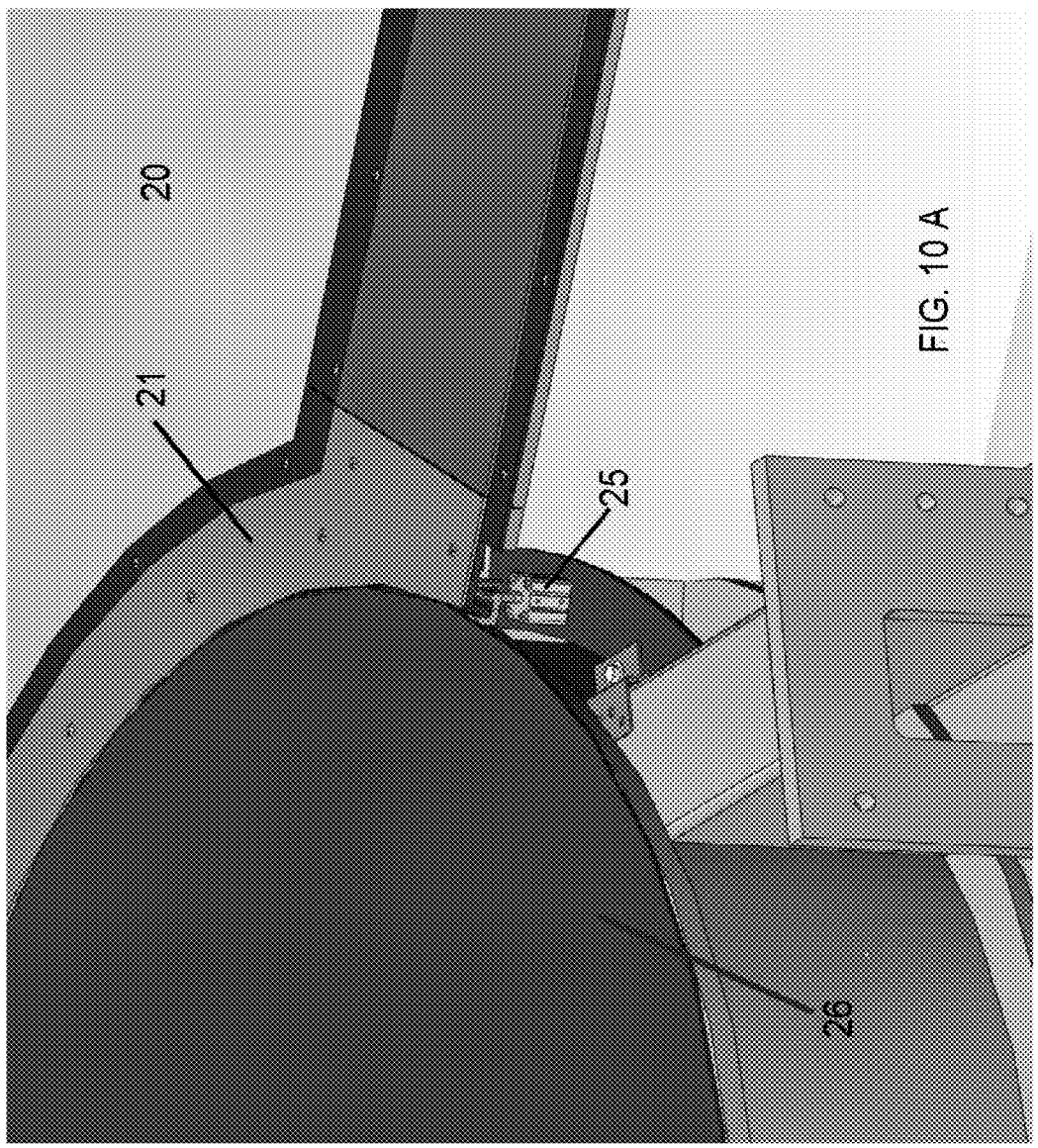
FIGS. 10A-C are depictions of retractable RF shield mechanism for a patient turntable, in accordance with features of the present invention.

A turntable RF seal 27 (as depicted in FIG. 2) is used to shield electromagnetic radiation emanating from the turntable system, so that the MRI scans have minimal interference. The mechanism is comprised of conductive metallic components and pneumatic parts. As depicted in FIGS. 10 A-C, the conductive components are used to make a conductive seal from the inner ring 26 of the turntable to an outer conductive ring 21 embedded in the floor 20. A means 25 for reversibly applying an EMF shield between the turntable and the floor is also provided. This means 25 is retractable to disengage the inner ring of the turn table from the outer ring 21.

The turn table RF sealing means comprises three main conductive parts. The outer ring 21 and inner ring 26 is made from a conductive material. The inner ring 26 remains in electrical communication with the mechanism of the turn table. The RF seal 25 is made from conductive material and is actuated by a pneumatic system which is supported by an underside region of the floor 20.

In order to move/align the patient surface between the MRI unit and LINAC system the RF seal channel (25) must be retracted. FIG. 10B depicts the sealing means 25 in a retracted configuration. This retraction allows the inner ring (26) to rotate inside the outer ring (21) for alignment of the patient surface. The design of the inner ring (26) and the outer ring (21) allow for contact between the two rings. This contact or overlap allows for the collection of debris and liquids which may fall between the two rings. Debris and liquids are not wanted in the MRI/LINAC room, so the design allows for easy removal and cleaning of the collection area.

The sealing means includes a actuating mechanism 128 comprising a piston 130 terminated at its distal or free end by a substrate engagement surface 132. The substrate engagement surface 132 defines a first upwardly extending protuberance 134 and a second upwardly extend protuberance 136. Intermediate the first and second protuberances is a partition 138 to prevent debris from settling within the cavities of the surface 132 defined by the flanking protuberances. The partition 138 is static relative to the surface, 132, but moves in tandem with the surface.

As depicted in FIG. 10C, when the piston 130 is extended, the tips of the protuberances contact the underside surfaces of the inner 20 and outer ring 21. Specifically, an upwardly facing surface 135 of the first protuberance 134 contacts the underside of the conductive MRI floor interface. Simultaneously, an upwardly facing surface 137 of the second protuberance contacts the underside of the conductive turntable cover plate 26. This contact establishes electrical communication between the turn table and the outer ring 2 thereby creating a continuous and contiguous electrical pathway 27 (and therefore electrical communication) with for the RF door seals located along the bottom edges of the doors. When the doors are closed and the turntable shield is actuated, the continuous electrical pathway between the turntable and the door seals provide RF shielding to the MRI from any electrical noise emanating from the LINAC.

When the MRI unit is going to be used to scan the patient the main door leaves will be closed along with the RF seals. This will include the turn table RF seal.

The turn table RF seal will be activated when the turn table is in the desired location that aligns the patient table with the MRI unit. When the turn table RF seal is activated/engaged the RF seal channel is moved by the pneumatic system to contact both the inner ring and outer ring to make a conductive seal across the two rings, which completes the RF seal of the room/enclosure. The RF seal channel is a secondary backup to collect debris and liquids.

An exemplary mechanism for the aforementioned bladder-activated electrical contact mechanism is found in U.S. Pat. No. 5,569,878, owned by the instant Assignee and incorporated in its entirety herein by reference.

A salient feature of the invention is that it enables both the MRI and the LINAC to share the same RF shielded room, but at different times of patient interaction. This is due to the space saving features of the EMI removable shield 16.

Figure 11:
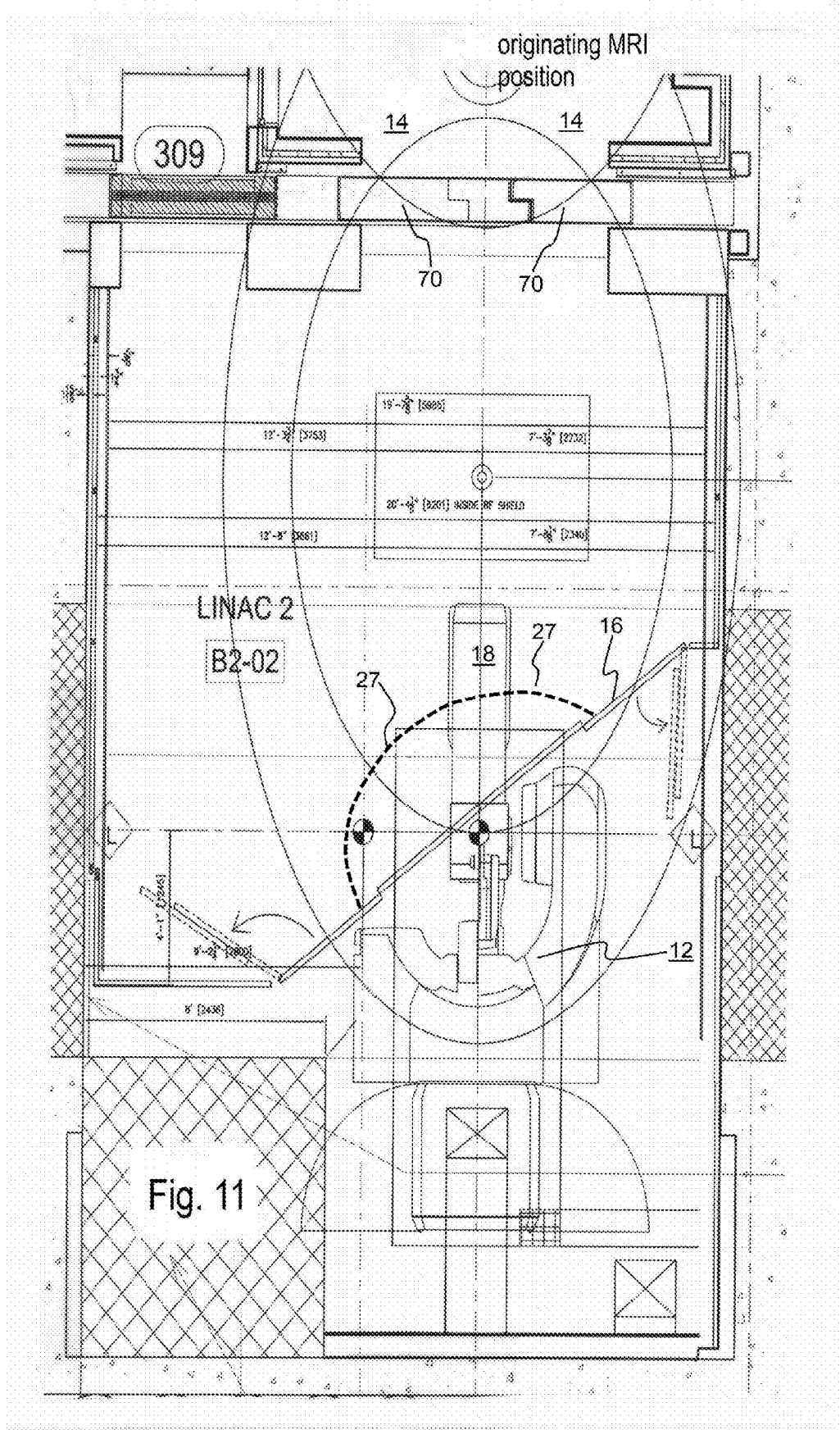
FIG. 11 is a plan view of the enclosure depicting the MRI and LINAC devices in their stowed positions, in accordance with features of the present invention.

In operation, a patient is placed on the patient support surface 18, such as a gurney or examination table. The table is already position within the enclosure 10, as depicted in FIG. 11 which is a plan view of an exemplary enclosure 10. The MRI machine 14 is seen in its original retracted position. A first step in the process, after the patient is placed on the table, is for the MRI doors 70 to open, and the MRI to enter the center of the room. The patient's position relative to the MRI is then adjusted by manipulating the patient support surface 18 along the x, y and z planes.

The next step in the process involves imaging of the patient with the now deployed MRI 14. It is during this step that the EMI removable shield 16 remains closed so as to shield the MRI from EMI emanating from the LINAC.

Once the MRI process is complete, the MRI equipment is withdrawn back to its original position behind the MRI doors, typically comprised of lead. Simultaneously, the EMI shield 16 is withdrawn and the LINAC treatment begins. The LINAC is not affected by the EMI emanating from the MRI. The invented configuration allows the retraction of the MRI equipment, opening of the EMI shield 16, and commencement of LINAC radiation treatment to occur all within a few minutes and preferably within 30-45 seconds after completion of patient imaging.

Laser/Door Positioning Detail

There are two pairs of lasers, one for the MRI positioning and one for the LINAC positioning. The doors are designed and positioned such that they will not interfere with the laser positioning system when needed. Once the MRI scan is complete and the technician knows the exact location of the treatment target, the laser positioning for the MRI is translated for the same position for the LINAC treatment. The doors will not interfere with the positioning capabilities for either of these procedures.

An embodiment of the invented enclosure further comprises wall-mounted laser positioning devices positioned such that the lasers remain intact no matter if the EMI removable shield 16 is fully deployed or fully nested. As such, the configuration of the sliding and swing doors is no more than 48" long, so as to maintain laser line of sight. As depicted in FIG. 2, a pair of opposing laser transmitter/receiver devices 80 are placed proximal to the LINAC zone and on lateral walls of the zone so as to facilitate patient positioning.

A second pair 82 of (opposing) laser beam devices is placed where the MRI magnet will advance and halt for the proper positioning for imaging of the patient. for that part of the treatment. The distance between these devices is a very specific empirically derived value and represents an optimum value of how close the MRI magnet can be to the LINAC area. The door leafs lengths are configured to work within that zone and not interfere with either of those beams. Since the pair of beams are not utilized simultaneously, the doors are placed in their specific modes (extended and fully closed during MRI imaging . . . or retracted out of the way during LINAC operation) allowing the particular active positioning beam to be unencumbered.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A radio frequency shield which reversibly transects an electromagnetic frequency enclosure, the shield comprising:
    a. a first plurality of panels attached to a first surface of the enclosure, wherein the first plurality is adapted to move through a first arc relative to the first surface, and also a first panel from said first plurality having a first leading edge capable of transecting the first arc;
    b. a second plurality of panels attached to a second surface of the enclosure, wherein the second plurality is adapted to move through an arc relative to the second surface of the enclosure, and also a second panel from said second plurality having a second leading edge capable of transecting the second arc so as to oppose the first leading edge; and
    c. a means for reversibly attaching the first leading edge to the second leading edge while simultaneously establishing electrical communication between the first and second plurality of panels.

2. The radio frequency shield as recited in claim 1 wherein each of said first and second plurality of panels comprises:
   a. a first leaf defining a first door surface and a second door surface, wherein the first leaf and the second leaf are in pivotal communication with the first surface of the enclosure;
   b. a second leaf defining a third door surface and fourth door surface, wherein each of said door surfaces are parallel to each other; and
   c. a means for facilitating the second leaf to slide relative to the first leaf.

3. The radio frequency shield as recited in claim 2 wherein the means for facilitating the second leaf to slide comprises a channel mounted to a third surface of the enclosure and adapted to receive a peripheral edge of the first leaf and second leaf.

4. The radio frequency shield as recited in claim 3 wherein the third surface comprises a header in which the plurality of panels nests, said header in electrical communication with the enclosure.

5. The radio frequency shield as recited in claim 1 wherein the means for reversibly attaching the first leading edge to the second leading edge comprises:
   a. a plurality of jaws mounted to the first opposing end of the first panel;
   b. a receiving end adapted to receive the first opposing end, wherein the receiving end is mounted to the second opposing end of the second panel;
   c. a cantilevered member in rotatable communication with the second opposing end;
   d. a means for simultaneously contacting the jaws to the second panel and extending the cantilevered member so as to establish an EMF shield between the first and second plurality of panels, above the first and second plurality of panels, and below the first and second plurality of panels.

6. A device for establishing electrical communication between a plurality of leaves and a room enclosure, the device comprising:
   a. a plurality of jaws mounted to a first opposing end of a first sliding door leaf;
   b. a receiving end adapted to receive the first opposing end, wherein the receiving end is mounted to a second opposing end of a second sliding door leaf;
   c. a cantilevered member in rotatable communication with the second opposing end; and
   d. a means for simultaneously contacting the jaws to the second sliding door leaf and extending the cantilevered member so as to establish an EMF shield between the leaves, above the leaves, and below the leaves.

7. The device as recited in claim 6 wherein the means for simultaneously contacting the jaws and extending the cantilevered member is a pneumatically-actuated bladder.

8. The device as recited in claim 6 wherein a distal edge of the cantilevered member terminates in an electrically-conductive webbing.

9. The device as recited in claim 6 further comprising an electrically conductive strip disposed intermediate each of said jaws and the second sliding door leaf, a proximal end of the strip electrically attached to the first opposing end, and a distal end of the strip in contact with the jaw.

* * * * *